United States Patent [19] — Merrill et al.

[11] Patent Number: 4,638,797
[45] Date of Patent: Jan. 27, 1987

[54] REINFORCED MOISTURE VAPOR PERMEABLE, PRESSURE-SENSITIVE ADHESIVE WOUND DRESSINGS

[75] Inventors: Richard E. Merrill, Sanbornton, N.H.; Craig L. Allard, Wakefield, Mass.

[73] Assignee: Acme United Corporation, Fairfield, Conn.

[21] Appl. No.: 855,586

[22] Filed: Apr. 23, 1986

[51] Int. Cl.$^4$ .............................................. A61L 15/00
[52] U.S. Cl. .................................................... 128/156
[58] Field of Search ............... 128/156, 155, 284, 287; 428/288

[56] References Cited

U.S. PATENT DOCUMENTS

| | | | |
|---|---|---|---|
| 4,186,233 | 1/1980 | Krajowski | 128/156 |
| 4,356,229 | 10/1982 | Brodnyan | 128/156 |
| 4,473,671 | 9/1984 | Green | 128/156 |
| 4,534,767 | 8/1985 | Habib | 128/156 |

Primary Examiner—Gregory E. McNeill
Attorney, Agent, or Firm—Mattern, Ware, Stoltz & Fressola

[57] ABSTRACT

By incorporating chemical reinforcing additives into a polyurethane resin base, a unique, reinforced moisture vapor permeable membrane is achieved which comprises a substantially increased modulus of elasticity, rendering the membrane easier to handle and employ. In the preferred embodiment, the polyurethane resin base comprises a blend of polyurethane resins and the two chemical reinforcing additives comprise a non-urethane copolymer resin and silica. Furthermore, a moisture vapor permeable, pressure-sensitive adhesive is applied to one surface of the membrane, thereby attaining a wound dressing which is easy to handle and employ for various surgical procedures.

15 Claims, No Drawings

REINFORCED MOISTURE VAPOR PERMEABLE, PRESSURE-SENSITIVE ADHESIVE WOUND DRESSINGS

TECHNICAL FIELD

This invention relates to moisture vapor permeable, pressure sensitive adhesive wound dressings, bandages, and surgical drapes, and more particularly to such wound dressings, bandages, and surgical drapes which comprise reinforced membranes for ease of handling.

BACKGROUND ART

During the last several years, there has been much activity in developing pressure sensitive adhesive, moisture vapor permeable wound dressings, bandages, and drapes for use in the medical field. It has been found that these moisture vapor permeable, pressure-sensitive adhesive dressings provide an improved surgical covering or bandage which speeds the natural wound healing process, while also protecting the wound site. In general, the wound dressings, bandages and surgical drapes allow water vapor to escape from a wound site while preventing liquid water from either entering or escaping from the site. In addition, bacteria is also prevented from passing through the wound dressing, thereby protecting the wound site from bacterial invasion.

Typically, these wound dressings, bandages, and surgical drapes all comprise a membrane layer which incorporates the desired physical characteristics to attain the moisture vapor permeability while preventing liquid water and bacteria from passing through the membrane. In addition, one surface of the membrane incorporates an adhesive which provides the desired pressure sensitive adherence for securing the membrane to the wound site and retaining the membrane in the desired position.

Although moisture vapor permeable, adhesive membranes have been widely recognized and accepted, with many competitive products being brought to the marketplace, all of these products have suffered from the same common deficiency. The principal problem is the difficulty users experience in handling and applying these prior art membranes to patients.

Moisture vapor permeable, pressure sensitive adhesive membranes are typically applied to a patient as a flat sheet, ranging in size from a few square inches to one or two square feet. In order to achieve the desired results, these moisture vapor permeable, pressure sensitive adhesive membranes are extremely thin and pliable. In this way, the desired permeability is provided and membranes are able to conform to the shape of the patient's body or skin. Unfortunately, this also causes the membranes to be extremely limp and difficult to handle.

In order to protect the adhesive surface, as well as allow the membranes to be easily handled prior to use, most prior art membranes incorporate comparatively heavy or thick release sheets or supporting or backing sheets. However, once the release or backing sheet has been removed, as is conventionally done prior to applying the adhesive membrane to the patient, great difficulty is encountered by the user, since the adhesive membrane is now unsupported and tends to stick to itself. As a result, most moisture vapor permeable, pressure-sensitive adhesive membranes require two individuals to apply the membrane to the patient, in order to assure and prevent the membrane from being so limp as to stick to itself and become unusable. These conventional prior art membranes are typified by Hodgson U.S. Reissue Pat. No. Re. 31,887 and the prior art references cited therein.

In an attempt to provide a system for applying these membranes to patients by one person, many prior art systems have been developed which provide a reinforcement or support means for the membrane in order to assist in the application of the membrane to a patient. These prior art systems include mechanical reinforcing layers such as foam, or other stiffening means, as well as removable layers of paper or cardboard, which assist in supporting the membrane during its application and are then removed once the membrane is in place. Furthermore, handles, both rigid and flexible, have been employed in order to further assist the operator in applying these membranes. The following U.S. Patents typify these prior art systems: U.S. Pat. Nos. 4,372,303 and 4,374,520.

Although these application and handling problems have existed for several years, no prior art system has been developed which achieves a readily dispensible, flat layered, vapor permeable, pressure-sensitive adhesive membrane which can be easily handled by a single individual and applied without difficulty. In general, the prior art systems which have been developed require the incorporation of additional support layers or stiffening layers to the membrane itself, typically on a non-adhesive surface thereof. However, these systems suffer from a tendency to degrade the quality of the membrane, as well as introducing extra material which may interfere with the healing process or with the visibility of the wound during its healing. Furthermore, in other such systems, the operator is faced with additional steps of removing the support or stiffening layer once the membrane has been in place, as well as the cumbersome nature of having to apply the membrane with this stiffening layer in place.

Therefore, it is a principal object of the present invention to provide a moisture vapor permeable, pressure-sensitive adhesive membrane which comprises a membrane layer incorporating reinforcing means therein which provides a membrane which is both inherently flexible, for application to the patient, and also sufficiently stiff to prevent the membrane from being limp and overly pliable during application.

Another object of the present invention is to provide a moisture vapor permeable, pressure-sensitive adhesive, reinforced membrane having the characteristic features described above which is easily used by a single individual and allows all reasonable sizes to be quickly applied to a patient without having the membrane stick to itself.

Another object of the present invention is to provide a moisture vapor permeable, pressure-sensitive adhesive, reinforced membrane having the characteristic features described above, which allows a rapid, easy, trouble-free application of the membrane to the wound site, regardless of the size, shape or length of the membrane.

A further object of the present invention is to provide a moisture vapor permeable, pressure-sensitive adhesive, reinforced membrane having the characteristic features described above which also assures complete sterility of the membrane for surgical use.

Another object of the present invention is to provide a moisture vapor permeable, pressure-sensitive adhesive, reinforced membrane having the characteristic features described above which prevents unwanted membrane stretching, while also providing an inherent visual indication to the operator when the membrane has been stretched beyond a satisfactory, acceptable limit.

Other and more specific objects will in part be obvious and will in part appear hereinafter.

DETAILED DISCLOSURE OF THE INVENTION

The present invention overcomes all of the prior art difficulties by attaining a totally new, unique membrane formulation. The membrane of the present invention comprises a dual-phase composition which incorporates a polyurethane base or carrier in combination with a substantial quantity of chemical additives which are uniformly dispersed throughout the entire polyurethane base to impart strength and rigidity to the membrane. In this way, a chemically reinforced membrane or film is attained.

By employing the membrane of the present invention, the difficulties experienced from using the limp, unreinforced, prior art membranes are all completely eliminated. With the present invention, a single individual is able to easily handle and apply all reasonable sizes of the moisture vapor permeable, pressure-sensitive adhesive membranes quickly and easily, without experiencing any difficulty or having to throw away the product due to such typical prior art difficulties as having the membrane stick to itself.

As is fully detailed below, the membrane of the present invention possesses a stiffness factor or a modulus of elasticity which is two to three times greater than the stiffness or modulus of elasticity of conventional prior art membranes. As a result of this substantially increased stiffness or rigidity, the reinforced, moisture vapor permeable, pressure-sensitive adhesive membrane of this invention eliminates the prior art drawbacks and provides a product which is easily handled by the user.

The reinforced membrane of the present invention is attained by employing a combination of a non-urethane resin and silica, as the chemical reinforcing additives which are combined with the polyurethane membrane base. Preferably, the non-urethane resin is selected from one of the following: a styrene-modified acrylic, an acrylic, a vinyl chloride-vinyl acetate copolymer, a phenoxy, or polyester. Although these various non-urethane resins can be employed, the preferred resin comprises a styrene-modified acrylic.

In its preferred embodiment, the reinforced membrane of the present invention comprises a single, homogeneous membrane layer or film which is constructed with a thickness typically used with wound dressings, bandages, and surgical drapes. In order to attain an easily usable wound dressing product, the reinforced film or membrane formulation of the present invention has a pressure-sensitive adhesive applied to one surface thereof. Most adhesives commonly employed on membranes in this art can be employed on the membrane of this invention with equal efficacy. Preferably, an acrylic type pressure-sensitive adhesive or a polyvinyl ether type adhesive is employed. In the preferred embodiment, the adhesive comprises an acrylic (hydroxy ethyl acrylate) sold under the trade name GELVA RH-737 by the Monsanto Company of Springfield, Mass. The product is typically supplied at 30–32% solids in a mixture of ethyl acetate, ethanol and toluene.

The adhesive can be applied to the membrane as either a continuous or discontinuous layer. If a continuous adhesive layer is desired, the adhesive will be applied to one entire surface of the membrane in order to attain the desired pressure-sensitive, continuous adhesive surface. Alternatively, if a discontinuous adhesive layer is desired, the adhesive is preferably applied to the membrane in a particular pattern, such as the negative of a dot pattern by screen printing, in order to impart the desired adhesive surface to the membrane. It has been found that coverage of at least 75% is preferred.

With the adhesive in place, all reasonable sizes of the reinforced membrane of this invention are easily handled by one person and securely applied to a patient, eliminating the prior art difficulties typically encountered with the unreinforced polyurethane films presently in use. In addition to the adhesive layer, a release sheet or backing layer is also employed to protect the adhesive as well as the membrane, until application of the membrane and adhesive to the patient is desired.

In practicing the teaching of this invention, the preferred silica employed in the polyurethane base or carrier comprises a fumed silica. Furthermore, based upon the combined weight of the silica and the polyurethane employed in the base or carrier, the quantity of silica employed ranges between about 0.5% and 15% by weight. The only difficulty that has been observed is that as the level of silica increases, the opacity of the resulting membrane also increases, as well as the viscosity of the composition. An increase in viscosity is realized since fumed silica acts as a thickening agent in an organic solvent system. Consequently, silica levels in excess of 15% by weight are considered to be unrealistic.

The quantity of styrene-modified acrylic which is employed in the polyurethane base or carrier can range from between about 1% to 50% of the combined weight of the styrene-modified acrylic and the polyurethane employed. However, when the styrene-modified acrylic exceeds 20% of the combined weight of the acrylic and polyurethane, the moisture vapor transmission rate of the resulting membrane is too low to be useful as a wound dressing for the present application. Consequently, although an enhanced reinforced membrane is attainable with a styrene-modified acrylic up to 50% of the combined weight of the acrylic and polyurethane, the more realistic upper limit for attaining a reinforced film for use as a wound dressing is about 20%.

By incorporating the preferred chemical reinforcing additives into the polyurethane base and applying the desired adhesive layer, in accordance with the present invention, a homogeneous, uniform, dual-phase, continuous, reinforced, pressure-sensitive adhesive membrane or film is attained which is capable of being easily handled in all reasonable sizes by a single individual without the undesirable limpness and membrane self-adherence which has plagued prior art constructions.

DESCRIPTION OF SPECIFIC EMBODIMENTS

By employing the teaching of the present invention, a homogeneous, uniform, dual-phase, continuous, reinforced, moisture vapor permeable, pressure-sensitive adhesive membrane is attained which completely eliminates the difficulties encountered with prior art membranes. As discussed above, the membrane of the present invention comprises a polyurethane base or carrier into which reinforcing chemical additives are incorporated in order to attain the desired reinforced membrane.

In addition to achieving an easily handled reinforced membrane, the present invention also attains a homogeneous, dual-phase membrane. The dual-phase characteristic of the membrane of the present invention is evidenced by membrane blushing or whitening which is observed at extreme strain levels. In addition to evidencing the dual-phase nature of the membrane of the present invention, this membrane blushing or whitening has been found to be extremely advantageous in providing the user with a visual indication that the membrane has been overstretched during the application process. As a result, whenever a blushing or whitening of the membrane is seen, the user automatically knows that the membrane should be thrown away, since it has been stretched to a greater extent than desirable.

The preferred membrane composition employs a polyurethane base or carrier into which chemical additives are combined in order to produce the desired reinforced membrane. In the preferred embodiment, the polyurethane employed to form the film or membrane base comprises a blend of Estane 5703 and Estane 5714F-1. Both of these products are manufactured by the B. F. Goodrich Company, Chemical Group, Cleveland, Ohio. Estane 5703 comprises a thermoplastic, polyester-based polyurethane resin which is one of the softest of this group of products, having a Shore hardness of 70A. The product is supplied as granules dusted with talc.

The Estane 5714F-1 is a thermoplastic, polyether based polyurethane resin which has a Shore hardness of 83A. This product is supplied as granules which are dusted with calcium stearate.

As discussed above, the preferred chemical additives which impart the reinforcement to the polyurethane based membrane comprises a combination of a non-urethane resin and silica. In the preferred embodiment, the non-urethane resin comprises a styrene/ethyl acetate/acrylic acid copolymer resin. The preferred styrene/ethyl acetate/acrylic acid copolymer resin is sold under the trade name GELVA RP-1215 by the Monsanto Company of Springfield, Mass. This product comprises a thermoplastic styrene/ethyl acetate/acrylic acid copolymer resin and is supplied in solution of 50% solids in toluene.

The preferred silica employed in the reinforced membrane of the present invention comprises a fine particle, high surface area fumed silica. The preferred silica is sold under the trade name CAB-O-SIL EH-5 by the Cabot Corporation, Cab-O-Sil Division, Tuscola, Ill. This product generally has an average particle size of 0.007 microns.

In order to assure that the reinforced membrane of the present invention comprises physical characteristics comparable to prior art unreinforced membranes, a listing of typical physical characteristics of prior art membranes was established. In Table I, this listing is presented. By employing this Table, the acceptability and operative equivalence of the membrane of the present invention and its various formulations was evaluated and the best product formulation was determined.

TABLE I

| Typical Characteristics of Moisture Vapor Permeable, Presssure-Sensitive Adhesive Membranes | |
|---|---|
| PHYSICAL PROPERTY | RANGE |
| Moisture Vapor Transmission Rate | 600–1,200 g/M2-day |

TABLE I-continued

| Typical Characteristics of Moisture Vapor Permeable, Presssure-Sensitive Adhesive Membranes | |
|---|---|
| PHYSICAL PROPERTY | RANGE |
| (MVTR) for Product | |
| Tensile Strength | 1,200 (min) psi |
| Elongation | 550–1,000% |
| Regain (50% strain only) | 98+% |
| $O_2$ transmission Rate | 500–1,000 cc/100 in2-day |
| Loop Tack | 500–2,000 grams |
| Ease of Release | 10–60 grams |
| Film Thickness | 1.0–2.0 mils |
| Adhesive Thickness | 1.0–1.5 mils |
| Product Thickness | 2.0–3.5 mils |

In order to assure that all physical properties of the various membranes were determined in a manner which would allow comparative analysis, the following standard test procedures were employed for all membrane tests.

Test Methods

1. Moisture Vapor Transmission Rate (MVTR)

Transmission of water vapor through the membrane is measured in accordance with ASTM Test E96-66, "Water Vapor Transmission of Materials in Sheet Form," except that a more suitable glass test container for small-area samples is employed. The conditions for the test are specified in Procedure E—temperature approximately 37.8° C. (100° F.), R.H. in dish approximately 0%, R.H. outside dish approximately 90%. The Test chamber (Hotpack Model 435300 Temperature-Humidity Chamber) is set at 38° C. dry Bulb, 36° C. wet bulb.

The glass container is a weighing bottle which is used without the stopper (Kimble 15145, 50 mm×25 mm diameter). The effective area of the opening, based upon measurement of I.D., is 3.85 cm². This is also the area of the exposed membrane under test.

To proceed with the test, a desiccant (Drierite, 8-mesh) is placed in the bottle to within 1 cm from the top. A square piece of membrane, adhesive side down, is carefully and evenly placed over the opening of the glass bottle, wrapped over the lip, and secured on the rim of the bottle with a rubber band. Excess membrane below the rubber band may be trimmed away. The unit is immediately weighed on an analytical balance to four decimal places.

The unit(s) is then promptly placed in the environmental chamber (zero time). The unit is weighed at 4 hours, 8 hours, and again at 24 hours. The data is plotted to confirm the weight gain is linear over 24 hours. The linear rate of gain R (in g/day) is $$R = \frac{\text{grams at end} - \text{grams at start}}{1 \text{ day}}$$

To obtain the MVTR for the product under test (in g/M2 day), $$MVTR_p = \frac{R}{3.8 \text{ cm}^2} \times 10,000$$

2. Tensile Strength and Elongation

Tensile strength is the maximum stress developed in the film material during tensile loading. Elongation is the measure of the material's ductility, or increase in gauge length until the point of rupture. This test was run according to ASTM-D228-73, Method A. The Instron tensile machine is used.

Prepare six samples (1"×4") of membrane product from which tensile and elongation measurements are obtained.

Set machine gauge length (distance between upper and lower jaws) at 1".

Clamp membrane (without backing) between jaws.

Run tensile load until failure (at a rate of 12"/min).

Calculate tensile strength in psi (load/cross-sectional area).

Measure elongation directly off recorder chart, adjusting the magnification factor (difference between crosshead speed and chart speed).

Record percent elongation at 100 gram, 200 gram, 400 gram, 800 gram, 1,000 gram loads, and percent elongation at failure.

3. Regain @ 50% Strain

This test, which is performed on the Instron machine, measures the ability of the membrane product to recover after being stretched to 50% of its original length. The test specimen must be accurately set up with gauge marks in order to obtain exact initial and final measurements between the gauge marks. A Vernier caliper is used for the measurements to the nearest 0.001". The samples in triplicate are stretched 50% in the Instron and allowed to relax (equilibrate) for 10 minutes before remeasuring the distance between the gauge marks.

$$\% \text{ Regain} = \frac{\text{Stretched Length} - \text{Final Length}}{\text{Stretched Length} - \text{Original Length}} \times 100$$

4. Oxygen Transmission Rate

The oxygen permeation test is carried out in accordance with ASTM D3895-81, "Method for Oxygen Gas Transmission Rate Through Plastic Film and Sheeting Using a Coulometric Sensor." The measurement is made using an Oxtran 10/50, an automatic multicell instrument manufactured by Modern Controls, Inc.

In accordance with the method, the sample film is mounted in a two-chambered gas transmission cell at atmospheric pressure. The "upstream" chamber is purged with dry, 99.5% pure oxygen while the "downstream" chamber is slowly purged by a stream of nitrogen gas. As oxygen permeates through the film into the nitrogen carrier gas, it is transported to a coulometric detector where it produces an electrical current, the magnitude of which is proportional to the amount of oxygen flowing into the detector per unit time.

The test conditions are set at a temperature of 37° C. and 0% R.H. The samples (5 cm$^2$) are run in triplicate. The oxygen transmission rates are determined after the samples have equilibrated in the dry test environment and measurements are taken until a steady state rate is achieved. This steady state rate is reported in units of cc $O_2$/100 in 2/day.

5. Adhesive Tack (Loop Test)

The purpose of the Loop Test is to determine the tack of the pressure-sensitive adhesive on the membrane. This test is adapted from Monsanto Company standard test procedures for pressure-sensitive adhesives (Gelva Bulletin No. 6358B). An Instron test machine is employed.

To reinforce the membrane so it can be handled, laminate the face side of the membrane to masking tape (supplied by Rexham).

Cut strips 1" wide×2-¾" long. Prepare at least three (3) strips from each sample.

Form a loop from the strip with the adhesive under test on the outside, and insert ¼" of each end of the loop into the upper jaw of the Instron.

Set a flat stainless steel plate (the Instron compression plate) into the lower jaw position.

Set the Instron crosshead speed at 5"/min (13 cm/min) and a travel limit in the "UP" mode of 0.25" between the plate and upper jaw.

Press the "UP" button to bring the plate in contact with the adhesive exposed at the bottom of the loop.

When the crosshead stops, press the "DOWN" button to draw the loop away from the steel plate.

Record the Loop Tack (in grams) from the recorder chart.

Report the average value from the samples.

6. Ease of Release

The ease of release from the backing is an important property of the permeable-membrane product. It is essential that the membrane peel away from the release backing easily and without stretching or distortion.

The Instron tensile machine is used to measure the peel strength of the pressure-sensitive adhesive from the release paper backing. This measurement is made using a "German Wheel" maintaining a constant 90° peel angle. In using the German Wheel method for peel, the release paper backing on the membrane product must be adhered to the wheel surface with double-sided adhesive tape. Once the specimen is in position on the wheel which forms the bottom jaw of the Instron, about 2" of the membrane is peeled by hand for clamping in the upper jaw. The sample size measures 1" wide by 10" in length with the peel measurement made over 8" of length on triplicate samples.

Instron conditions:
Crosshead Speed—12"/min
Chart Speed—6"/min
Full Chart Scale—100 gms

7. Thickness

Thickness measurements are made using a digital linear gauge (Ono Sokki EG-307 with a 3/16-inch diameter flat foot, 6-0z measuring force).

8. Modulus of Elasticity

Modulus (stiffness) is an alternate term for modulus of elasticity which is often used in connection with rubber and elastomers. Since polyurethane is well known as an elastomer, this property is particularly applicable. The modulus of elasticity is determined according to ASTM D638-72. It is the rate of change of strain as a function of stress and is taken from the slope of the initial linear portion of the load-extension curve.

The Instron tensile machine is used.

Prepare three samples (1"×4") of membrane product.

Set machine gauge length (distance between upper and lower jaws) at 1".

Clamp membrane (without release backing) sample between jaws.

Run tensile load until failure (at a rate of 12"/min).

Draw straight line tangent to initial linear portion of resulting load-extension curve.

This modulus is calculated by dividing the difference in stress corresponding to a certain section on the straight line (tangent) by the corresponding difference in strain; i.e., Modulus (E)=stress/strain. The values are computed using the average initial cross-section area of the test specimen.

The last test procedure details the manner in which the modulus of elasticity of each membrane was determined. This test is of particular importance, since the modulus of elasticity or stiffness of the membrane represents a critical physical characteristic which is employed to prove the superiority of the reinforced membranes of the present invention over prior art unreinforced membranes.

The substantially increased modulus of elasticity achieved by the membranes of this invention identifies a significant advance made by the present invention over prior art membranes, which are characterized by being limp and difficult to handle. Consequently, the modulus of elasticity is not listed in Table I.

As is readily determined from the following examples, the membranes of the present invention possess a modulus of elasticity or stiffness which is significantly greater than the modulus of elasticity of prior art membranes. This allows all reasonable sizes of the membrane of this invention to be easily handled by a single individual, eliminating all of the difficulty presently encountered with prior art membranes. The substantial increase in the modulus of elasticity or stiffness of the membranes of the present invention clearly shows that a unique, reinforced membrane construction is attained, and a substantial improvement over all of prior art membranes is realized.

EXAMPLES

For illustrative purposes only, and not intended in any way to be limiting, the following examples present various membrane formulations that can be employed to attain a reinforced, moisture vapor permeable, pressure-sensitive adhesive membrane, possessing a modulus of elasticity or stiffness which allows the membrane to be easily handled. In each example, the membrane formulation is provided in detail. However, in comparing these detailed formulations with the previous discussion, it must be remembered that the reinforcing additives have been described as a percent of the total quantity of the polyurethane and the particular additive employed in the formulation.

EXAMPLE 1

One of the preferred compositions of the membrane of the present invention is detailed in Table II. In this formulation, the fumed silica represents about six percent by weight of the combined weight of the silica and the polyurethane base, while the styrene-modified acrylic represents about nine percent by weight of the combined weight of the styrene-modified acrylic and the polyurethane base.

TABLE II

| Material | Quantity (grams) |
| --- | --- |
| Estane 5703 | 9.5 |
| Estane 5714F-1 | 9.5 |
| Tetrahydrofuran | 42 |
| Methyl ethyl ketone | 38 |
| Gelva RP-1215 (50%) | 4 |

TABLE II-continued

| Material | Quantity (grams) |
| --- | --- |
| Cab-O-Sil EH-5 | 1.2 |

This membrane was prepared by first dispersing the Cab-O-Sil EH-5, in methyl ethyl ketone (MEK). This dispersion was achieved by ball milling for about five hours to break up the agglomerates. If desired, other methods may be employed to obtain a good, agglomerate-free dispersion of the silica. Next, the Gelva RP-1215 resin solution was added directly to a mixture of the Estane 5703 resin and the Estane 5714 F-2 resin. In addition, the Cab-O-Sil EH-5 and methyl ethyl ketone dispersion was added along with the additional required amounts of methyl ethyl ketone and tetrahydrofuran (THF). The entire composition is then mixed until the Estane resins are completely dissolved.

The methyl ethyl ketone is a well known solvent for Estane resins, having a boiling point of 80° C. (171° F.) and a flash point of −9° C. (16° F.). A suitable methyl ethyl ketone can be obtained from several industrial sources. The tetrahydrofuran employed in this composition is a solvent for Estane resins having a boiling point of 64° C. (147° F.) and a flash point of −14.5° C. (6° F.). This solvent is also well known and can be obtained from several industrial sources.

Once the membrane composition was completed, the membrane itself was formed by cutting a piece of casting paper to a convenient size. In general, six inches by thirteen inches was found to be desirable. The casting paper was then placed on a vacuum plate and secured by suction. With the aid of a four inch wide, fifteen mil film applicator, a wet film of the membrane composition was drawn over the entire length of the casting paper. The coated paper was then set aside to dry in the air for about two to three hours. When completed, the dry film of the membrane formulation was formed.

In order to achieve and test a complete wound dressing, the adhesive was applied to the membrane. The adhesive was applied to the membrane by first cutting a piece of release paper to a desirable size. It was found that release paper having dimensions of about six inches by ten inches was desirable. The release paper was then placed, silicone-treated side up, on a vacuum plate and then secured by suction.

Using a four inch wide, five mil film applicator, a wet film of the adhesive was drawn over the entire length of the release paper. The adhesive employed was the preferred adhesive detailed above which is the acrylic (hydroxy ethyl acrylate) sold by Monsanto Company of Springfield, Mass. under the trade name GELVA RH-737. Once coated, the release paper and adhesive film were set aside to dry in the air for about two to three hours.

Once the drying time was completed, the membrane and adhesive were laminated together. In order to achieve this lamination, the membrane and casting paper were placed with the membrane side up on a smooth, clean surface. The adhesive and release paper were then centered and aligned over the membrane, with the adhesive side down. Once in position, the adhesive and release paper were placed onto the membrane. Using a rubber roller, the sections were squeezed together by moving the roller from one end to the other. Preferably, at least three passes were made with the rubber roller in order to eliminate any air pockets.

Once completed, upon removal of the casting paper, the samples were trimmed to the desired size and set aside for at least twenty-four hours at 72° F. in fifty percent relative humidity before testing or inspection.

EXAMPLE 2

Another preferred composition for the reinforced membrane of the present invention is detailed in Table III. In this membrane formulation, the fumed silica is about six percent by weight of the combined weight of the silica and the polyurethane base, while the styrene-modified acrylic is about thirteen percent by weight of the combined weight of the styrene-modified acrylic and the polyurethane base.

TABLE III

| Material | Quantity (grams) |
| --- | --- |
| Estane 5703 | 9.5 |
| Estane 5714F-1 | 9.5 |
| Tetrahydrofuran | 42 |
| Methyl ethyl ketone | 38 |
| Gelva RP-1215 (50%) | 6 |
| Cab-O-Sil EH-5 | 1.2 |

This membrane was formulated in substantially the identical manner described above in reference to Example 1, with the increased quantity of the styrene-modified acrylic being employed.

EXAMPLE 3

In order to provide a membrane sample for use as a control, a control membrane was made using the process detailed in Example 1. However, as shown in Table IV, the control membrane employed only the polyurethane resins and the solvents, without any reinforcing additives.

TABLE IV

| Material | Quantity (grams) |
| --- | --- |
| Estane 5703 | 9.5 |
| Estane 5714F-1 | 9.5 |
| Tetrahydrofuran | 42 |
| Methyl ethyl ketone | 38 |

In order to prove the efficacy of the present invention and the increased handling ease which was realized from the membranes of Example 1 and Example 2, the physical properties of the membranes of these two examples were determined. These properties were then compared to the physical properties of the control membrane of Example 3. This comparative analysis is shown in Table V.

TABLE V

| Physical Test Properties of Membrane Products | | | |
| --- | --- | --- | --- |
|  | Example 1 | Example 2 | Example 3 |
| 1. MVTR for Product (g/M²-day) | 867 | 761 | 931 |
| 2. Tensile Strength (psi) | 1,655 | 2,042 | 1,863 |
| 3. Elasticity (% Elongation at Load) | | | |
| 100 g | 9 | 6 | 17 |
| 200 g | 17 | 12 | 43 |
| 400 g | 91 | 41 | 239 |
| 800 g | 319 | 252 | 411 |
| 1,000 g | 383 | 338 | 454 |
| 4. Elongation at Failure (%) | 630 | 683 | 675 |
| 5. % Regain (50% Extension) | 98.2 | 98.5 | 98.5 |
| 6. Oxygen Transmission Rate (cc/24 hr-100 in²-Atm) | 672 | 521 | 789 |
| 7. Loop Tack (grams) | 661 | 623 | 886 |
| 8. Ease of Release (grams) | 13 | 13 | 13 |
| 9. Product Thickness (mils) | 2.6 | 2.7 | 2.5 |
| 10. Modulus of Elasticity (Stiffness) (psi) | 1,587 | 2,053 | 791 |

By reviewing the physical properties of the membrane of Example 1 and Example 2 and comparing these properties to the properties of the control membrane, it is readily apparent that the membranes defined in Examples 1 and 2 comprise all of the desirable physical properties of the control membrane, and are well within the physical specifications of Table I for a moisture vapor permeable, pressure-sensitive adhesive membrane. The one significant difference detailed in Table V is the substantial increase in the modulus of elasticity or stiffness which is attained by the membranes of Example 1 and Example 2.

As shown in Table V, Example 1 comprises an increased modulus of elasticity which is about 200 percent greater than the modulus of elasticity of the control membrane. Furthermore, the membrane of Example 2 is almost 260% greater than the control membrane. Clearly, the substantial increase in the modulus of elasticity for each membrane is proof that the membranes of Example 1 and Example 2 are reinforced polyurethane membranes, which are easily handled during use and application, and also have all of the requisite characteristics required for a moisture vapor permeable, pressure-sensitive adhesive membrane.

EXAMPLE 4

A further composition for the reinforced membrane of the present invention is detailed in Table VI. In this membrane formulation, the non-urethane copolymer resin comprises a styrenated acrylic, with the membrane formulation incorporating about sixteen percent by weight of the styrenated acrylic to the combined weight of the polyurethane and the styrenated acrylic. In this formulation, the styrenated acrylic employed is sold under the trade name Desoto E-327 which is manufactured by Desoto Inc., of Des Plaines, Ill. This product is supplied at sixty percent solids in toluene. In this formulation, the fumed silica employed is about six percent by weight of the combined weight of the silica and the polyurethane.

TABLE VI

| Material | Quantity (grams) |
| --- | --- |
| Estane 5703 | 9.5 |
| Estane 5714F-1 | 9.5 |
| Tetrahydrofuran | 42 |
| Methyl ethyl ketone | 38 |
| Desoto E-327 (60%) | 6 |
| Cab-O-Sil EH-5 | 1.2 |

The membrane was made using the process detailed above in reference to Example 1.

EXAMPLE 5

A still further composition for the reinforced membrane of the present invention is detailed in Table VII. In this membrane formulation, a styrenated acrylic is employed as the non-urethane copolymer resin. However, in this example, about thirteen percent by weight of a styrenated acrylic resin was used as compared to the combined weight of the styrenated acrylic and the polyurethane. In addition, Desoto E-326 was used, which is manufactured by Desoto Inc. of Des Plains, Ill. This product is supplied in solution of fifty percent solids in toluene. The fumed silica employed in this formulation is about six percent by weight of the combined weight of the silica and the polyurethane.

TABLE VII

| Material | Quantity (grams) |
|---|---|
| Estane 5703 | 9.5 |
| Estane 5714F-1 | 9.5 |
| Tetrahydrofuran | 42 |
| Methyl ethyl ketone | 38 |
| Desoto E-326 (50%) | 6 |
| Cab-O-Sil EH-5 | 1.2 |

As with the previous examples, this membrane was formulated using the process detailed above in Example 1.

In order to show the efficacy of the membranes of Examples 4 and 5, the more pertinent physical properties of these membranes were determined. The comparative test results achieved from these membrane samples are shown in Table VIII.

TABLE VIII

| | Example IV | Example V |
|---|---|---|
| 1. MVTR for Product (g/M$^2$-day) | 1135 | 1098 |
| 2. Tensile Strength (psi) | 1790 | 1882 |
| 3. Elasticity (% Elongation at Load) | | |
| 100 | 6 | 5 |
| 200 | 15 | 12 |
| 400 | 125 | 92 |
| 800 | 409 | 357 |
| 1,000 | 497 | 446 |
| 4. Elongation at Failure (%) | 1015 | 784 |
| 5. Product Thickness (mils) | 2.3 | 2.3 |
| 6. Modulus of Elasticity (Stiffness) (psi) | 2083 | 1895 |

It will thus be seen that the objects set forth above, among those made apparent from the preceding description, are efficiently attained and, since certain changes may be made from the above article, without departing from the scope of the present invention, it is intended that all matter contained in the above description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Particularly, it is to be understood that in said claims, ingredients or compounds recited in the singular are intended to include compatible mixtures of such ingredients wherever the sense permits.

Having described our invention, what we claim as new and desire to secure by Letters Patent is:

1. A homogeneous, reinforced, moisture vapor permeable, pressure-sensitive adhesive wound dressing comprising
    A. a reinforced membrane film or layer incorporating a homogeneous blend of
        a. at least one thermoplastic polyurethane resin,
        b. a non-urethane copolymer resin, and
        c. silica; and
    B. a moisture vapor permeable, pressure sensitive adhesive applied to one surface of said membrane film or base, whereby a reinforced, moisture vapor permeable, pressure sensitive adhesive wound dressing is achieved which possesses a substantially increased modulus of elasticity, imparting greater stiffness and rigidity to the wound dressing for increased handling ease.

2. The homogeneous, reinforced, moisture vapor permeable, pressure-sensitive adhesive wound dressing defined in claim 1, wherein said non-urethane resin is further defined as comprising one selected from the group consisting of a styrene-modified acrylic, an acrylic, a vinyl chloride-vinyl acetate copolymer, phenoxy and polyester.

3. The homogeneous, reinforced, moisture vapor permeable, pressure-sensitive adhesive wound dressing defined in claim 2, wherein said silica is further defined as comprising fumed silica.

4. The homogeneous, reinforced, moisture vapor permeable, pressure sensitive adhesive wound dressing defined in claim 1 wherein said adhesive is further defined as comprising one selected from the group consisting of acrylic type and polyvinyl ether type.

5. The homogeneous, reinforced, moisture vapor permeable, pressure-sensitive adhesive wound dressing defined in claim 1, wherein said polyurethane is further defined as comprising at least one selected from the group consisting of thermoplastic polyester based polyurethane resins and thermoplastic polyether based polyurethane resins.

6. A reinforced, moisture vapor permeable, pressure-sensitive adhesive wound dressing comprising
    A. a reinforced membrane film or layer incorporating a dual phase, homogeneous blend of
        a. at least one thermoplastic polyurethane resin,
        b. a styrene-modified acrylic comprising between about one percent and fifty percent by weight of the combined weight of the styrene-modified acrylic and the polyurethane resin, and
        c. a fumed silica comprising between about 0.5 percent and fifteen percent by weight of the combined weight of the silica and the polyurethane resin; and
    B. a moisture vapor permeable, pressure-sensitive adhesive applied to one surface of said membrane film or base whereby a reinforced, moisture vapor permeable, pressure-sensitive wound dressing is achieved which possesses a substantially increased modulus of elasticity, imparting greater stiffness and rigidity to the wound dressing for increased handling ease.

7. The homogeneous, reinforced, moisture vapor permeable, pressure-sensitive adhesive wound dressing defined in claim 6, wherein said adhesive is further defined as comprising one selected from the group consisting of acrylic type and polyvinyl ether type.

8. The homogeneous, reinforced, moisture vapor permeable, pressure-sensitive adhesive wound dressing defined in claim 6, wherein said polyurethane is further defined as comprising a blend of substantially equal quantities of a thermoplastic polyester based polyurethane resin and a thermoplastic polyether based polyurethane resin.

9. The homogeneous, reinforced, moisture vapor permeable, pressure-sensitive adhesive wound dressing defined in claim 6, wherein said adhesive is further defined as comprising an acrylic type adhesive which is applied to one surface of the reinforced membrane film as a continuous layer.

10. The homogeneous, reinforced, moisture vapor permeable, pressure-sensitive adhesive wound dressing defined in claim 6, wherein said adhesive is further defined as comprising an acrylic type adhesive which is applied to one surface of said reinforced membrane film as a discontinuous layer.

11. The homogeneous, reinforced, moisture vapor permeable, pressure-sensitive adhesive wound dressing defined in claim 10, wherein said discontinuous adhesive layer is further defined as covering at least 75% of the surface of said reinforced membrane film.

12. The homogeneous, reinforced, moisture vapor permeable, pressure-sensitive adhesive wound dressing defined in claim 6, wherein the fumed silica is further defined as comprising about 6 percent by weight of the combined weight of the silica and the thermoplastic polyurethane resin.

13. The homogeneous, reinforced, moisture vapor permeable, pressure-sensitive adhesive wound dressing defined in claim 12, wherein said styrene-modified acrylic is further defined as comprising between about 3 percent and 20 percent by weight of the combined weight of the styrene-modified acrylic and the polyurethane resin.

14. The homogeneous, reinforced, moisture vapor permeable, pressure-sensitive adhesive wound dressing defined in claim 12, wherein said styrene-modified acrylic is further defined as comprising a thermoplastic styrene/ethyl acetate/acrylic acid copolymer resin comprising between about 9 percent and 13 percent by weight of the combined weight of the styrene-modified acrylic and the thermoplastic polyurethane resin.

15. A reinforced, moisture vapor permeable, pressure-sensitive wound dressing comprising:
  A. a reinforced membrane film or layer incorporating a dual phase, homogeneous blend of
    a. substantially equal quantities of a thermoplastic polyester based polyurethane resin and a thermoplastic polyether based polyurethane resin,
    b. a styrene/ethyl acetate/acrylic acid copolymer resin comprising between about 9 percent and 13 percent by weight of the combined weight of the polyurethane resins and the non-urethane copolymer resin, and
    c. a fumed silica comprising about 6 percent by weight of the combined weight of the silica and the polyurethane resins; and
  B. a moisture vapor permeable, pressure-sensitive acrylic type adhesive applied to one surface of said reinforced membrane film whereby a reinforced, dual-phase, homogeneous, moisture vapor permeable, pressure-sensitive wound dressing is achieved which possesses a substantially increased modulus of elasticity, imparting greater stiffness and rigidity to the wound dressing for increased handling ease.

* * * * *